US00PP25576P2

(12) United States Plant Patent
Vanderhaegen

(10) Patent No.: US PP25,576 P2
(45) Date of Patent: May 26, 2015

(54) ***RHODODENDRON* PLANT NAMED 'HORT09'**

(50) Latin Name: *Rhododendron simsii*
Varietal Denomination: HORT09

(71) Applicant: Johan Vanderhaegen, Kruishoutem (BE)

(72) Inventor: Johan Vanderhaegen, Kruishoutem (BE)

(73) Assignee: HortiBreed NV, Lochristi (BE)

( * ) Notice: Subject to any disclaimer, the term of this patent is extended or adjusted under 35 U.S.C. 154(b) by 71 days.

(21) Appl. No.: 13/987,208

(22) Filed: Jul. 11, 2013

(51) Int. Cl.
*A01H 5/02* (2006.01)

(52) U.S. Cl.
USPC ..... Plt./238

(58) Field of Classification Search
CPC ..... A01H 5/00
USPC ..... Plt./238
See application file for complete search history.

*Primary Examiner* — June Hwu
*Assistant Examiner* — Keith Robinson

(57) ABSTRACT

A new cultivar of *Rhododendron* plant named 'HORT09' that is characterized by dark shiny green leaves, purple flowers and early flowering.

1 Drawing Sheet

Botanical classification: *Rhododendron simsii.*
Variety denomination: 'HORT09'.

BACKGROUND OF THE INVENTION

The present invention relates to a new and distinct cultivar of *Rhododendron* plant botanically known as *Rhododendron simsii* and hereinafter referred to by the cultivar name 'HORT09'.

The new cultivar is the product of a breeding program conducted by the inventor in a cultivated area of Kruishoutem, Belgium. The objective of the breeding program is to develop new *Rhododendron* cultivars that have long lasting flowers and bright green leaves.

'HORT09' is a hybrid that originated from the hybridization of the female or seed parent *Rhododendron simsii* 'Flamenco' (not patented) and the male or pollen parent a proprietary selection of *Rhododendron simsii* identified as '01025' (not patented). The crossing was conducted in 2005. The cultivar 'HORT09' was selected by the inventor in December of 2007 as a single plant within the progeny of the stated cross in a greenhouse environment of Kruishoutem, Belgium.

Asexual reproduction of the new cultivar 'HORT09' by stem cuttings was first performed in December of 2007 in Kruishoutem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'HORT09'. These traits in combination distinguish 'HORT09' as a new and distinct cultivar.

1. *Rhododendron* 'HORT09' exhibits dark shiny green leaves.
2. *Rhododendron* 'HORT09' exhibits purple flowers.
3. *Rhododendron* 'HORT09' exhibits early flowering.

The closest comparison varieties are *Rhododendron* 'Ostalette' (not patented) and 'Christine Matton' (U.S. Plant Pat. No. 11,693).

'HORT09' is different than 'Ostalette' in having lighter purple double flowers and an earlier flowering period. In contrast, the flowers of 'Ostalette' are darker purple and are semi-double.

'HORT09' is different than 'Christine Matton' in having purple flowers. In contrast, the flowers of 'Christine Matton' are pink.

'HORT09' is distinguishable from the female parent 'Flamenco' by the following characteristics:

1. 'HORT09' exhibits glossy green leaves. The leaves of 'Flamenco' are dull green.
2. 'HORT09' exhibits double flowers. The flowers of 'Flamenco' are semi-double.
3. 'HORT09' exhibits a larger overall flower size than the flower size of 'Flamenco'.

'HORT09' is distinguishable from the male parent '01025' by the following characteristics:

1. 'HORT09' exhibits purple flowers. The flowers of '01025' are red.

BRIEF DESCRIPTION OF THE DRAWING

The accompanying photograph illustrates the distinguishing traits of *Rhododendron* 'HORT09'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'HORT09'. Data was collected in Kruishoutem, Belgium from 24 month old greenhouse grown plants in 1.0 liter containers. The time of year was Spring and the average temperature was 22° Centigrade during the day and 18° Centigrade at night. The light level was 5000 Klux and there were no photoperiodic treatments. Color determinations are in accordance with The Royal Horticultural Society Colour Chart 2001 edition, except where general color terms of ordinary dictionary significance are used. The growing requirements are similar to the species. 'HORT09' has not been tested under all possible conditions and phenotypic differences may be observed with variations in environmental, climatic, and cultural conditions, however, without any variance in genotype.

Botanical classification: *Rhododendron simsii* 'HORT09'.

Use: Ornamental Perennial Shrub.

Parentage: 'HORT09' is a hybrid of the female or seed parent *Rhododendron simsii* 'Flamenco' and the male or pollen parent a proprietary selection of *Rhododendron simsii* identified as '01025'.

Vigor: Moderate.

Growth rate: Approximately 8 cm. in height and 15 cm. in width per year.

Growth habit: Broad Upright, densely branched.

Plant shape: Flattened globose.

Suitable container size: 1.0 liter container.

Height: Average 27 cm. in height.

Width: Average 40 cm. in width.

Hardiness: USDA Zone 9. (between 0° C.-40° C.)

Propagation: Stem Cuttings.

Time to initiate roots: Approximately 30 days to produce roots on an initial cutting.

Time to produce a rooted cutting or liner: Approximately 60 days.

Root system: Fine and fibrous.

Root color: N155A and 199C.

Stem:

*Branching habit*.—Freely branching.
*Average number of lateral branches*.—6.
*Pinching*.—Yes.
*Lateral branch diameter*.—3 cm. in diameter.
*Lateral branch length*.—11 cm. in length.
*Lateral branch strength*.—Moderately strong.
*Stem color*.—144B.
*Pubescence*.—Dense.
*Internode length*.—8 mm. between nodes.
*Shape*.—Round.
*Surface*.—Dull.
*Stem strength*.—Moderately strong.

Foliage:

*Texture* (*both surfaces*).—Glossy, slightly leathery.
*Leaf arrangement*.—Alternate, clustered towards the top of the stems.
*Compound or single*.—Single.
*Quantity of leaves per lateral branch*.—22.
*Leaf shape*.—Elliptic to obovate.
*Leaf apex*.—Mucronulate.
*Leaf base*.—Attenuate.
*Leaf length*.—5 cm. in length.
*Leaf width*.—2 cm. in width.
*Pubescence*.—Absent.
*Leaf margin*.—Entire.
*Vein pattern*.—Pinnate.
*Young leaf color* (*upper surface*).—141A.
*Young leaf color* (*lower surface*).—141B.
*Mature leaf color* (*upper surface*).—139A.
*Mature leaf color* (*lower surface*).—138A.
*Vein color* (*lower surface*).—141B.
*Vein color* (*upper surface*).—138D.
*Leaf attachment*.—Petiolate.
*Petiole dimensions*.—7 mm in length, slightly flattened 2 mm. in width, 1 mm in height.
*Petiole color*.—141B.
*Durability of foliage to stress*.—Moderate.

Flower:

*Flower arrangement*.—Terminal clusters.
*Inflorescence dimensions*.—6 cm. in diameter and 3.5 cm. in height.
*Flowering habit*.—Continuously once a year.
*Flower type*.—Double.
*Quantity of flowers per lateral stem*.—Approximately 2.
*Quantity of flower buds per lateral stem*.—Approximately 1-5.
*Quantity of flowers and buds per plant*.—Approximately 60.
*Flowering season*.—December to April.
*Time to flower or response time*.—2 to 4 weeks depending on temperature regime.
*Rate of flower opening*.—After the first flower of a cluster has opened, all flowers of that cluster will open in approximately 14 days.
*Fragrance*.—None.
*Self-cleaning or persistent*.—Persistent.
*Flower bud length*.—9 mm. in length.
*Flower bud diameter*.—7 mm. in diameter.
*Flower bud shape*.—Ovate.
*Flower bud color*.—141B.
*Rate of bud opening*.—10 days.
*Flower aspect*.—Upright.
*Flower shape*.—Open funnel shape.
*Flower dimensions*.—6 cm. in diameter and 3.5 cm. in height.
*Flower longevity*.—Lasts approximately 24 days on plant.
*Petal appearance*.—Dull, slight velvety.
*Petal texture*.—Glabrous.
*Petal arrangement*.—Funnelform, rosette, double.
*Number of petals*.—Five in number.
*Petals fused or unfused*.—Fused.
*Petal shape*.—Irregular obovate.
*Petal margin*.—Entire.
*Petal apex*.—Rounded.
*Petal base*.—Fused.
*Petal dimensions*.—2.5 cm. in length and 2.1 cm. in width.
*Petal color when opening* (*upper side*).—71B.
*Petal color when opening* (*under side*).—71B.
*Petal color when fully opened* (*upper side*).—71B.
*Petal color when fully opened* (*under side*).—71B.
*Petal color fading to*.—Not fading.
*Number of petaloids*.—Five.
*Petaloid shape*.—Irregular obovate.
*Petaloid margin*.—Entire.
*Petaloid apex*.—Rounded.
*Petaloid color*.—71B (both sides).
*Petaloid dimensions*.—0.75 cm. in length and 0.60 cm. in width.

Calyx:

*Calyx shape*.—Rounded.

Sepals:

*Sepal appearance*.—Dull, pubescent.
*Number of sepals*.—Five in number.

*Sepals fused or unfused*.—Unfused.
*Sepal shape*.—Ovate.
*Sepal margin*.—Entire.
*Sepal apex*.—Acute.
*Sepal base*.—Rounded.
*Sepal dimensions*.—8 mm. in length and 3 mm. in width.
*Sepal color when opening* (*upper side*).—141B.
*Sepal color when opening* (*under side*).—141B.
*Sepal color mature* (*upper side*).—141B.
*Sepal color mature* (*under side*).—141B.

Bracts: Absent.

Pedicels:
*Pedicel dimensions*.—0.5 cm in length and 2 mm. in diameter.
*Pedicel color*.—141B.
*Pedicel strength*.—Moderate.

Reproduction organs:
*Stamen number*.—1.
*Anther shape*.—Fused to petals.
*Anther color*.—71B.
*Pistil number*.—1.
*Pistil dimension*.—2.0 cm. in length.
*Stigma shape*.—Round.
*Stigma color*.—N88A.
*Ovary color*.—144B.

Fruit and seed: Fruit and seed production has not been observed.

Disease and pest resistance: Plants of the new *Rhododendron* have not been observed for disease or pest resistance.

The invention claimed is:

1. A new and distinct variety of *Rhododendron* plant named 'HORT09' as described and illustrated.

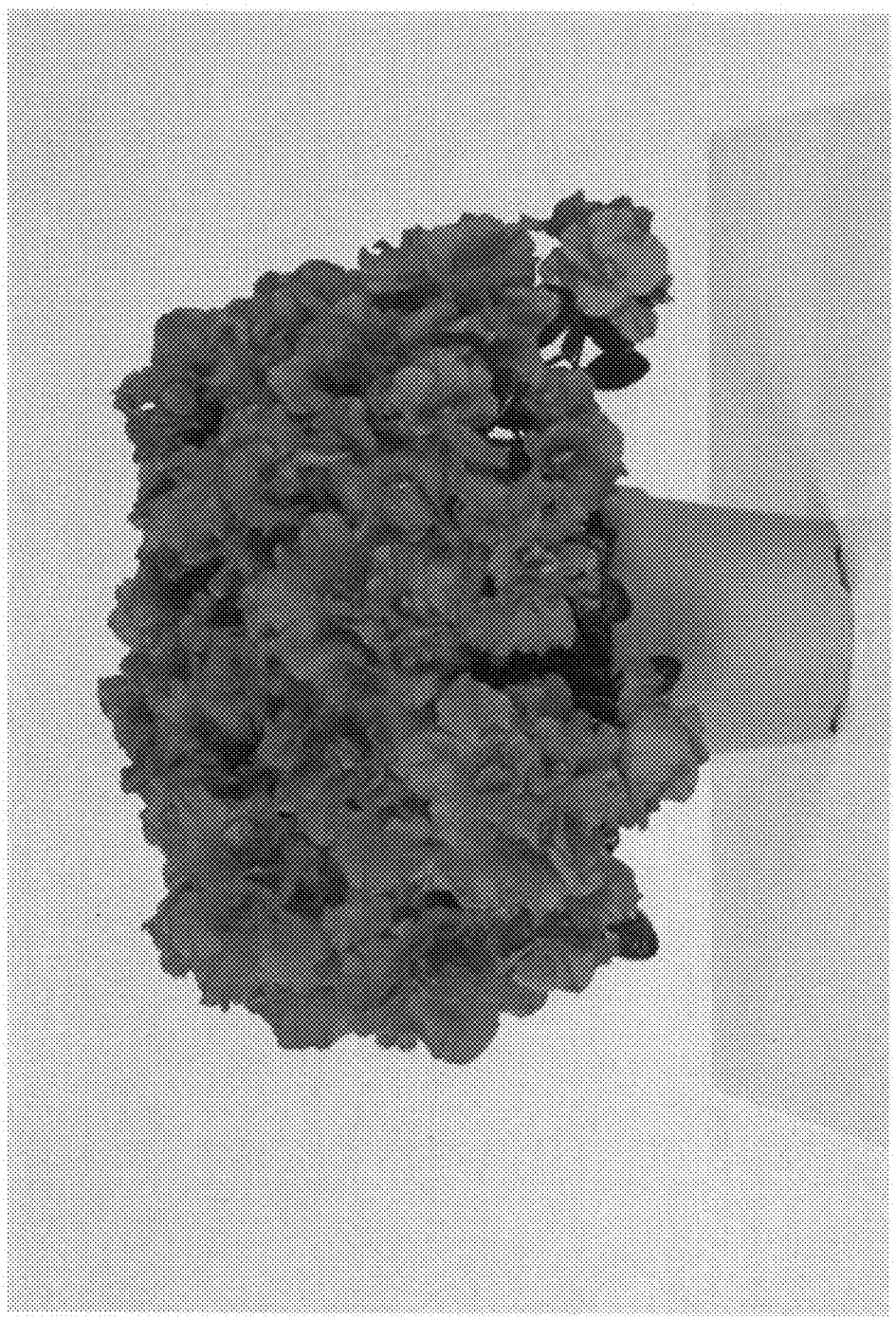

* * * * *